United States Patent [19]

Doi et al.

[11] 4,421,382
[45] Dec. 20, 1983

[54] FIBER RETAINING DEVICE FOR POWER LASER

[75] Inventors: Yuzuru Doi, Niza; Teruyuki Kakeda; Noriaki Kawamura, both of Tokyo, all of Japan

[73] Assignee: Asahi Kogaku Kogyo Kabushiki Kaisha, Tokyo, Japan

[21] Appl. No.: 241,440

[22] Filed: Mar. 6, 1981

[30] Foreign Application Priority Data

Apr. 1, 1980 [JP] Japan .................... 55-43223[U]

[51] Int. Cl.³ .......................................... G02B 7/26
[52] U.S. Cl. ........................ 350/96.20; 350/96.21
[58] Field of Search ............... 350/96.20, 96.21, 96.26; 250/227; 128/4-9, 11, 303.15

[56] References Cited

U.S. PATENT DOCUMENTS 624,392  5/1899  Smith ..................... 350/96.20
3,878,397  4/1975  Robb et al. ............. 250/227

Primary Examiner—David K. Moore
Assistant Examiner—Robert E. Wise

[57] ABSTRACT

A retaining device having a cylindrical centering portion and a conical chucking portion for holding a bundle of optical fibers for use with a medical laser scalpel.

1 Claim, 4 Drawing Figures

FIBER RETAINING DEVICE FOR POWER LASER

DETAILED DESCRIPTION OF THE DEVICE

The present invention relates to a retaining device for retaining the incident end of a bundle of optical fibers for a power laser to be used for a medical laser scalpel.

Since a centering member and a chucking member are disposed separately of each other as means for retaining the incident end of a bundle of optical fibers for a power laser according to the prior art, those two members have to be separately mounted in a sliging tube. Moreover, since the through hole formed in the centering member for guiding the fiber bundle is machined to have a larger diameter than that of the fiber bundle itself, there is a fear that the center of the chucking member in its chucking operation is misaligned from the center of the centering member so that the highly accurate centering operation of the fiber bundle cannot be effected.

In order to eliminate the drawbacks concomitant with the prior art, the present device contemplates to provide a fiber retaining device, in which a centering member and a chucking member are constructed into an integrally molded fiber retainer and in which this fiber retainer is integrally machined with a through hole for a bundle of optical fibers so that the center of the centering portion may not be misaligned from that of the chucking portion and so that the assembly may be facilitated.

BRIEF DESCRIPTION OF THE DRAWING

The present device will be described in more detail in the following in connection with the embodiment thereof. In FIG. 1, reference numeral 3 indicates a cylindrical lens mount guide ring, to the incident end 3a of which a condensing lens 1 is fixed. Numeral 7 indicates a tapped hole for a later-described stop screw. In FIG. 2, there is shown a sliding tube 6 which is to be slidably fitted in the lens mount guide ring 3. Said sliding tube 6 is formed at its radial center portion with a through hole 6d for a bundle 2 of optical fibers and at its incident end (at the lefthand side of the drawing) with an internal thread 6c, from which a larger hole 6a having a larger diameter than that of the aforementioned through hole 6d is formed to have a predetermined length while being machined at a midway portion into the so-called "tapered hole" 6b of a converging shape merging into the through hole 6d. At the incident end of the sliding tube 6, there is mounted a fiber retainer 4 for the fiber bundle 2, which is to be inserted and fitted in the larger hole 6a and the tapered hole 6b. The fiber retainer 4 is shown in a perspective view in FIG. 3. Said fiber retainer 4 is formed into such a bullet shape as has its radial center formed with a through hole for the fiber bundle 2. The fiber retainer 4 is machined on the outer circumference of its intermediate portion to have a reduced external diameter and from its intermediate portion to a chucking portion 4b to have a larger internal diameter. The incident end of the retainer 4 is formed into a cylindrical centering portion 4a whereas the emanating end of the same is formed into the chucking portion 4b having a frustoconical shape. Incidentally, said chucking portion 4b is formed with a plurality of slits so that it can provide the chucking portion 4b having a spring action according to the machined shape of the aforementioned intermediate portion. As has been described in the above, the fiber retainer 4 is integrally molded of the centering portion 4a and the chucking portion 4b. Indicated at numeral 5 is a holding threaded ring for the retainer 4, which is to be brought into meshing engagement with the aforementioned internal thread 6c. The retainer 4 has its centering portion 4a and chucking portion 4b fitted in the larger hole 6a at the incident end and the tapered hole 6b of the sliding tube 6, respectively, and is fixed in the sliding tube 6 by means of the holding threaded ring 5. The fiber bundle 2 is inserted through the through hole 6d of the sliding tube 6 into the the through hole for the fiber bundle 2, which is positioned on the center axis of the retainer 4. When it is intended to retain the fiber bundle 2, the chucking portion of the retainer 4 is squeezed along the tapered hole 6b of the sliding tube 6, as the retainer 4 is forced toward the emanating end by means of the holding threaded ring 5, so that the fiber bundle 2 can be retained on the center axis without any fail.

FIG. 4 shows the overall construction of the retaining device thus far described. The aforementioned sliding tube 6 is inserted into the lens mount guide ring 3 and is so adjusted that the incident end of the fiber bundles comes to the plane where a laser beam 10 coming from a power laser head 9 is condensed by the action of the lens 1. After that, the sliding tube 6 is fixed by means of a stop screw 8 or the like. The emanating end of the sliding tube 6 is connected with the emanating end of a medical laser scalpel through a cover tube 11 which is made of a flexible material so that a laser beam 12 may be emitted.

Figure 1:
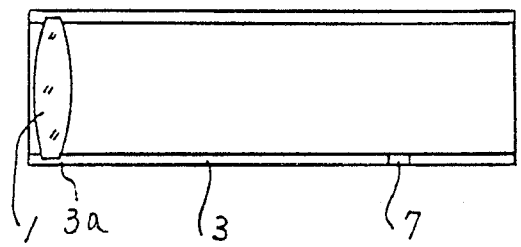
FIG. 1 is a sectional view of a lens mount guide ring taken on the center axis.
Figure 2:
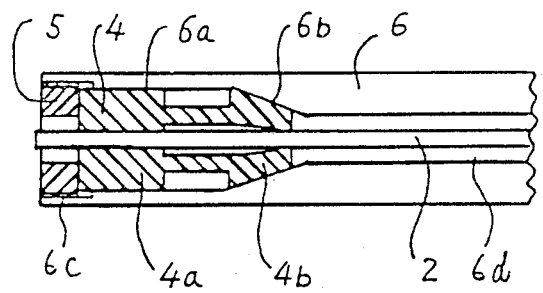
FIG. 2 is a axially sectional view showing the incident end of a sliding tube according to one embodiment of the present device.
Figure 3:
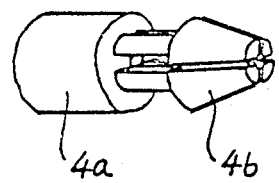
FIG. 3 is a perspective view showing a fiber retainer.
Figure 4:
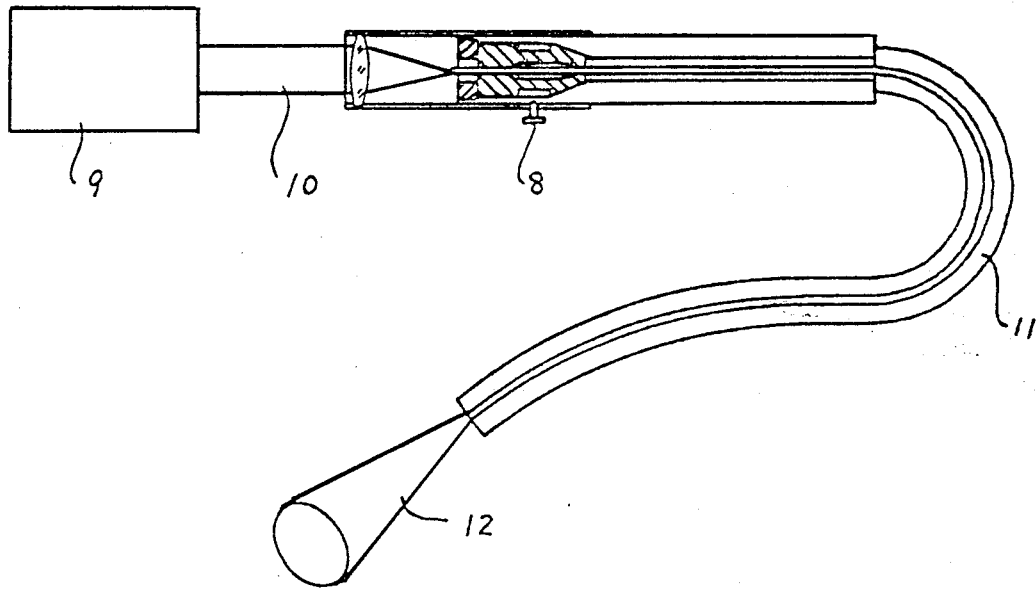
FIG. 4 is a simplified sectional view showing the overall construction of the retaining device according to the present device when it is mounted at the incident end of a medical laser scalpel.

As has been described hereinbefore, according to the present device, since the centering portion and the chucking portion are integrally molded, their assembly can be facilitated, and the fiber bundle can be chucked on the center axis without any fail. There can be attained another remarkable effect that the construction is so simplified to reduce the size and the production cost.

We claim:

1. A medical laser scalpel comprising:
    a cylindrical lens mount guide sleeve,
    a lens mounted proximate a first end of said sleeve,
    a cylindrical tube received in a second end of said sleeve and slidably retained therein, said tube being formed with a through-hole having a frusto-conical section formed at an intermediate section thereof and having internal threads formed proximate one end thereof,
    an integrally molded fiber retainer positioned within the through-hole of said cylindrical tube for holding and accurately centering a bundle of optic fibers, said fiber retainer including a cylindrical centering member having a central hole, a frusto-conical chucking member spaced from said centering member having a central hole aligned with the central hole in said centering member and a plurality of slits extending along the length thereof and inwardly from the surface thereof, a holding ring coupled to said cylindrical member having external threads formed thereon enmeshed with the internal threads formed in the cylindrical member securing said retainer in said cylindrical tube and for urging said frusto-conical chucking member into engagement with the frusto-conical portion of said through-hole to urge the sides of said frusto-conical member together to retain and accurately center a bundle of fibers in said retainer and said tube.

* * * * *